United States Patent [19]
Jacobson

[11] Patent Number: 5,818,703
[45] Date of Patent: Oct. 6, 1998

[54] DC/DC CONVERTER FOR A VARIABLE VOLTAGE LOAD

[75] Inventor: Peter Jacobson, Haguenau, France

[73] Assignee: ELA Medical S.A., Montrouge, France

[21] Appl. No.: 287,834

[22] Filed: Aug. 9, 1994

[30] Foreign Application Priority Data

Aug. 10, 1993 [FR] France .................................. 93-09807

[51] Int. Cl.$^6$ .............................................. H02M 3/335
[52] U.S. Cl. .............................................................. 363/21
[58] Field of Search ................................. 363/15, 16, 20, 363/21, 23, 25

[56] References Cited

U.S. PATENT DOCUMENTS

| | | | |
|---|---|---|---|
| Re. 26,652 | 8/1969 | Mirowski et al. | 128/419 D |
| Re. 27,757 | 9/1973 | Mirowski | 128/419 D |
| 4,037,271 | 7/1977 | Keller | 363/21 |
| 4,316,472 | 2/1982 | Mirowski et al. | 128/419 D |
| 4,541,039 | 9/1985 | Sandler | 363/21 |
| 4,548,209 | 10/1985 | Wielders et al. | 128/419 D |
| 4,577,268 | 3/1986 | Easter et al. | 363/21 |
| 4,614,192 | 9/1986 | Imran et al. | 128/419 D |
| 4,800,883 | 1/1989 | Winstrom | 128/419 D |
| 4,823,796 | 4/1989 | Benson | 128/419 D |
| 4,827,936 | 5/1989 | Pless et al. | 128/419 D |
| 5,091,837 | 2/1992 | Duspiva et al. | 363/15 |
| 5,430,405 | 7/1995 | Cohen | 327/581 |

OTHER PUBLICATIONS

Patent Abstracts of Japan, vol. 15, No. 98 (E–1042) 8 Mars. 1991 & JP–A–02 307 361 (ELCO CO LTD) 20 Dec. 1990.

*Primary Examiner*—Matthew V. Nguyen
*Attorney, Agent, or Firm*—Orrick, Herrington & Sutcliffe

[57] ABSTRACT

A DC/DC converter circuit to convert input source energy to output load energy, for example, a flyback converter to charge a defibrillation storage capacitor from a low-voltage battery in an implantable cardiac defibrillator. The converter allows input current to flow in the flyback inductor for a fixed time, and it allows output current to flow for a time directly proportional to average battery voltage and inversely proportional to the voltage on the capacitor being charged. When used near an electromagnetic communication link, to avoid interference, a control circuit enables and disables the converter at a maximum frequency that is substantially below the operating frequency of the communication link. In addition, the control circuit restricts the converter to transfer energy at a minimum fundamental frequency substantially above the frequency of the communication link.

16 Claims, 3 Drawing Sheets

DC/DC CONVERTER FOR A VARIABLE VOLTAGE LOAD

FIELD OF THE INVENTION

This invention relates to DC/DC converter circuits, more particularly to converter circuits operating with variable load voltage, such as capacitor charging circuits, and even more particularly to converter circuits operating a circuit for charging the high energy shock storage capacitor in an implantable defibrillator, from a battery. The invention also relates to minimizing interference between a DC/DC converter and an electromagnetic communication link, for example, an electromagnetic communication link for an implanted cardiac control device.

BACKGROUND OF THE INVENTION

DC/DC converter circuits with variable load voltage commonly store energy in an inductor, to adapt input to output voltage with only parasitic losses. As used herein, the term "inductor" refers to a single coil (winding), multiple coils with a common terminal (autotransformer), multiple coils with no common terminal (isolation transformer), and to combinations of any of the foregoing.

Here a defibrillator refers to any device intended to revert (to interrupt, terminate or stop) a tachyarrhythmia or a fibrillation with electrical energy substantially exceeding the pacing energy provided by implantable cardiac pacemakers. This includes implantable defibrillator/cardioverter/pacemakers and implantable defibrillator/pacemakers.

Here the high energy storage capacitor of a defibrillator can include one capacitor, or more than one capacitor connected in series, parallel, or both.

Implantable defibrillators generally deliver a truncated capacitor discharge shock with a maximum voltage of approximately 0.75 KV. These devices employ low voltage batteries, on the order of 3 to 15 V, as their primary power supply. They then must include a circuit to transfer energy from the battery to the high voltage capacitor by converting the battery voltage to energy sufficient to charge the capacitor. This circuit should operate with high efficiency, to preserve battery life. It should also charge the capacitor or capacitors as rapidly as possible, to permit delivering defibrillation therapy as early and as often as possible after the patient's condition requires it.

Capacitor charging circuits in the known art frequently employ a flyback converter, due to its efficiency and simplicity. A typical flyback converter operates with a two-part cycle and includes an inductor. During the first part of the cycle, called the input phase, current increases in the inductor, storing energy in its magnetic field. During the second part of the cycle, called the output phase, current decreases in the inductor, transferring energy to the output load. A series diode prevents energy from flowing to the load during the input phase.

At the start of the input phase, a control circuit closes a switch applying an input source voltage to a winding of the inductor. The voltage across the winding causes current to ramp up in the winding, storing energy in a magnetic field in the inductor. The slope of the ramp increases in direct proportion to input source voltage.

At the end of the input phase, the control circuit opens the switch between the input source and the inductor winding. The energy stored in the field causes current to continue to flow through any available path including an inductor winding. The flyback circuit offers only the path including the series diode and the load. Thus, the inductor transfers energy to the load. The inductor output current ramps down until either no more energy remains in the inductor, or the controller closes the input switch and starts current ramping up again.

The slope of the ramp during the output phase increases in direct proportion to load voltage, for example, in direct proportion to the voltage of the energy storage capacitor load which the converter charges. Thus, the time it takes to transfer a given amount of energy from the input source to the inductor during the input phase depends inversely on input source voltage, and the time it takes to transfer this energy from the inductor to the load during the output phase depends inversely on load voltage.

In the background art, Mirowski US RE27652 and US RE27757 refer to a means for automatically defibrillating, with a DC/DC converter, an input source consisting of a battery at approximately 15 V, and an output load consisting of a capacitor charged from 0 to 2.5 KV. Mirowski enables the converter by closing a relay which connects the input source to the converter, but gives no details about the converter itself.

Mirowski U.S. Pat. No. 4,316,472, Pless U.S. Pat. No. 4,827,936 and Benson U.S. Pat. No. 4,823,796 refer to a converter with a means to enable and disable converter energy selectively when the voltage on the storage capacitor reaches a predetermined or preprogrammed value.

Imran U.S. Pat. No. 4,614,192 refers to a charging circuit wherein the RF emissions from a charging transformer carry charging information to an external demodulator and decoder, to provide a readout of implanted device performance for a physician.

Wielders U.S. Pat. No. 4,548,209 refers to a flyback converter operating at a fixed frequency with variable input phase duration. The control circuit starts the input phase on every leading edge of a fixed frequency clock. It ends the input phase either when primary current exceeds a preset value below inductor saturation, or at a fixed time before the next clock edge, or at a second shorter fixed time if it finds the battery voltage is below a preset value.

Winstrom U.S. Pat. No. 4,800,883 refers to a flyback converter operating with fixed input phase duration and variable frequency. The control circuit starts the input phase after either a fixed maximum output phase duration, or when the inductor voltage falls during the output phase, indicating that no energy remains in the inductor.

It is apparent that a converter which charges the energy storage capacitor in an implantable defibrillator requires a control circuit to enable selective charging to reach and hold a predetermined target voltage. A controller for a flyback converter further needs to set input and output phase durations to avoid inductor saturation, to prevent drawing too much current from the battery and thus lowering battery voltage, and to adjust for the decreasing time it takes to transfer a given amount of energy to the storage capacitor as that capacitor charges. The converter also should not interfere with a nearby electromagnetic communication link between the implant and an external programming and readout device. The background art addresses these objectives, but with deficiencies:

1. The circuits disclosed in Mirowski U.S. RE27652 and U.S. RE27757 require a bulky and potentially unreliable electromechanical relay to enable charging selectively. Moreover these patents do not teach how to implement the converter.

2. The circuit of Imran U.S. Pat. No. 4,614,192 conveys only a one-bit binary communication signal (charger operating or not) to an external readout device. In more modern implantable devices, a separate electromagnetically-coupled link communicates with an external programming and readout device. The improvements over Imran include bidirectionality and the ability to convey a variety of stored or realtime digital and analog information about the implant. However, the use of an inductance in a converter in an implant with an electromagnetic communication link must address the problem of interference from the converter to the link.

3. The circuits of Mirowski U.S. Pat. No. 4,316,472, Pless U.S. Pat. No. 4,827,936 and Benson U.S. Pat. No. 4,823,796 employ a semiconductor switch to enable charging selectively, but do not teach how to implement the converter. Moreover, their circuits for enabling charging show no means for insuring that the charger operates for at least some minimum time each time the circuit calls for charging, and stops for some minimum time each time the circuit indicates charging is complete. In fact, no prior art circuit for selectively enabling converter operation restricts the frequency at which the enabling circuit changes state. When the storage capacitor reaches full charge, the charger needs to "top up" the capacitor by running from time to time to replace energy lost to leakage and to voltage measurement circuits. These charging circuits operate at many amperes, with rates of change up to a hundred amperes per microsecond. Consequently, they produce magnetically coupled interference at their fundamental operating frequency, and also at the frequency of activity, i.e., selective enabling and disabling. To reduce magnetically coupled interference, especially with an electromagnetic communication link, selective enabling and disabling should occur at a frequency substantially below the link carrier or operating frequency.

4. The flyback circuit of Wielders U.S. Pat. No. 4,548,209, operating at fixed frequency with variable input phase duration, seems inappropriate for an application with variable secondary load voltage. At beginning of charging, when it takes a long time to transfer stored energy from the inductor to the capacitor, Wielders points out that the circuit begins the input phase with energy still in the inductor. Consequently, the inductor current starts from a nonzero value during the input phase, and Wielders needs to shorten the input phase to maintain the same peak stored energy and avoid saturating the inductor. Operating the input switch while current flows in the inductor increases losses in that switch. Conversely at end of charging, when it takes a short time to transfer stored energy from the inductor to the capacitor, the magnetic field may fall to zero before the controller restarts the input phase. This "dead time" when no current flows adds needlessly to total time required to charge the energy storage capacitor.

5. The circuit of Winstrom U.S. Pat. No. 4,800,883, operating at fixed input phase duration and variable frequency, seems more appropriate for capacitor charging than the Wielders circuit. However, Winstrom sets the end of the output phase by measuring the change in inductor voltage resulting from collapse of the magnetic field when the inductor has completed transferring its energy to the storage capacitor. The amplitude of this signal varies directly with load voltage. Moreover, this signal includes high-frequency alternating current components due to resonance of the secondary winding inductance and primary leakage inductance with secondary parasitic capacitance (which is especially pronounced when using bifilar secondary windings, as Winstrom recommends).

Both the Wielders circuit (which measures inductor current to set the end of the input phase) and the Winstrom circuit (which measures inductor voltage to set the end of the output phase) rely on measurement of signals with very rapid rates of change. Bringing such signals onto an integrated circuit preferably used for implementing the charger controller in an implantable device creates magnetic and capacitive coupling problems. Moreover, Winstrom must deal with a trigger signal varying in amplitude directly as the storage capacitor charges, and including resonance components, requiring additional circuitry to extract valid timing information.

SUMMARY OF THE INVENTION

Broadly, the present invention provides an improved DC/DC converter design for variable voltage loads. Among the improvements are:

1. Operating a flyback converter with fixed input phase duration, and adjusting the output phase duration to correspond to the time necessary to transfer all energy stored in the inductor to the load, without requiring measurement of any rapidly changing signals.

2. When used nearby an electromagnetic communication link, setting the minimum fundamental frequency of the converter substantially above the operating frequency of that link.

3. When used intermittently nearby an electromagnetic communication link, selectively enabling and disabling converter operation at a maximum frequency substantially below the operating frequency of that link.

In a preferred embodiment, a timing control circuit (herein "timer") is used to control the input current switch in a flyback converter. The timer provides fixed input phase duration (switch on-time) and variable output phase duration (switch off-time). When operating the converter intermittently, the timer operates for a minimum time, and ceases to operate for a minimum time, corresponding to a frequency substantially below the operating frequency of the telemetry link.

The timer sets a maximum output phase duration to maintain the flyback operation frequency substantially above the telemetry link frequency. When possible, without violating this minimum frequency constraint, the timer sets the output phase to a value proportional to an average input source voltage and inversely proportional to the output load voltage. As a result, the output phase ends just at the moment when the energy stored in the inductor falls to zero. This is because the amount of magnetic flux stored during the input phase varies in direct proportion to the input source voltage, and the time it takes to reduce this flux to zero varies in direct proportion to the peak flux and in inverse proportion to the load voltage. Average input source voltage and the output load voltage change very slowly, over many converter cycles, permitting simple measurement circuits.

Another aspect of the present invention is directed to a DC/DC converter which includes:

means for inductively storing energy, namely an inductor;
switch means for selectively enabling the inductor input current;
a diode means for enabling the inductor output current only when the inductor input current is substantially zero;
timing means for repeatedly cycling the switch means to close for a first duration and then to open for a second duration; and
an output compensating means for adjusting said second duration in inverse proportion to the output load voltage.

According to other characteristics of this converter, the output load voltage may be an average or a peak output load voltage. The timing means is preferably a timing control circuit having a first monostable means for timing the first duration, a second monostable means for timing the second duration, and the output compensating means includes a logic means for alternately and repeatedly operating the first and second monostable means to form an astable oscillator with a period essentially equal to the sum of said first and second durations. The second monostable means includes a timing capacitor, means for resetting the timing capacitor to a first preset voltage when the logic means does not operate the second monostable means, threshold means for determining when the voltage across the timing capacitor reaches a preset threshold voltage, output compensating means for charging or discharging the timing capacitor toward the threshold voltage at a current essentially proportional to the output load voltage, and means for indicating completion of the second duration to said logic means, activated by the threshold means.

The output compensating means for charging or discharging is preferably a resistor connected between the output load voltage and the terminal of the timing capacitor connected to said threshold means.

In an alternate embodiment, an input compensating means for adjusting the second duration in direct proportion to the input source voltage also may be provided. The input source voltage may be an average or a peak input source voltage. In this embodiment, the timing control circuit includes the first monostable means for timing the first duration, and the second monostable means for timing the second duration, in which the second monostable means includes the output compensating means and the input compensating means, and logic means for alternately operating the first and second monostable means to form an astable oscillator with a period essentially equal to the sum of said first and second durations.

In one particular embodiment, the second monostable means includes a timing capacitor, means for resetting the timing capacitor to a first preset fraction of said input source voltage, when the logic means does not operate said second monostable means, threshold means including the input compensating means for determining when the voltage across said timing capacitor reaches a threshold voltage equal to a preset fraction of the input source voltage, output compensating means for charging or discharging the timing capacitor toward the threshold voltage with a current essentially proportional to output load voltage, and means for indicating completion of the second interval to the logic means, which is activated by the threshold means.

In accordance with the present invention, the first duration for closing said switch means is preferably a fixed preset value.

The switch means is preferably connected in series between the positive terminal of the input source voltage and the inductor. More preferably, the switch means is a transistor switch, such as a p-channel metal-oxide-semiconductor field-effect-transistor (MOSFET).

Another aspect of the invention concerns a DC/DC converter which repeatedly transfers energy from an input source to an output load at a fundamental frequency, with means for selectively enabling converter operation, and the converter is used near an electromagnetic communication link. One such converter includes:

means for restricting the converter fundamental frequency to a minimum frequency that is substantially higher than the carrier frequency of the communication link, and means for restricting the frequency of changes of the state of the means for selectively enabling converter operation, i.e., when the converter is operating and not operating, to a maximum frequency substantially lower than the carrier frequency of the communication link.

Preferably, such a converter includes an inductor means for storing energy, a switch for selectively enabling inductor input current, a diode means, e.g., a diode or diode network for enabling inductor output current only when the inductor input current is substantially zero, and a timer for repeatedly cycling the switch to close for a first duration and then to open for a second duration, at a fundamental frequency, a means for restricting the fundamental frequency to a minimum frequency substantially higher than the carrier frequency of the link, and output compensating means for adjusting said second duration in inverse proportion to output load voltage.

The timer preferably includes a first monostable circuit for timing the first duration at a substantially fixed value, a second monostable circuit for timing the second duration, including said means for restricting the fundamental frequency and including the output compensating means, and control logic to operate alternately said first and second monostable circuits and to form an astable oscillator with a period that is essentially equal to the sum of said first and second durations.

The second monostable circuit preferably includes:

a timing capacitor, means for resetting said timing capacitor to a first preset voltage when said control logic does not cause second monostable means to function, threshold means for determining when the voltage across the timing capacitor reaches a preset threshold voltage, output compensating means for charging or discharging the timing capacitor toward the threshold voltage at a current essentially proportional to the output load voltage, means for restricting the fundamental frequency by charging or discharging the timing capacitor toward the threshold voltage with an additional current essentially independent of output load voltage, and means for indicating completion of the second duration to the control logic, activated by the threshold means.

Alternatively, the timer has timing means including a first monostable circuit for timing said first duration, a second monostable circuit for timing said second duration, including said means for restricting fundamental frequency, said output compensating means, and said input compensating means, and logic means for alternately operating said first and second monostable circuits to form an astable oscillator with a period that is essentially equal to the sum of said first and second durations.

In this alternate version of the timer, the second monostable circuit includes a timing capacitor, means for resetting the timing capacitor to a first preset fraction of the input source voltage when the logic means does not operate said second monostable circuit, threshold means including input compensating means for determining when the voltage across said timing capacitor reaches a voltage threshold equal to a preset fraction of said input source voltage, output compensating means for charging or discharging the timing capacitor with a current essentially proportional to the output load voltage, means for restricting said fundamental frequency by charging or discharging the timing capacitor toward said threshold voltage with an additional current essentially independent of output load voltage, and means for indicating completion of said second duration to the logic means, activated by said threshold means.

The means for restricting the frequency of changes of state preferably includes a latch clocked by a fixed frequency clock, where the fixed frequency is substantially lower than the carrier frequency of the communication link.

The converter of the present invention is preferably applied to charging an energy storage capacitor of an implantable defibrillator.

BRIEF DESCRIPTION OF THE DRAWINGS

Further features of the invention, its nature, and various advantages, will be more apparent from the accompanying drawings and the following detailed description of the invention, in which like reference characters refer to like elements, and in which.

DETAILED DESCRIPTION OF THE INVENTION

Figure 1:
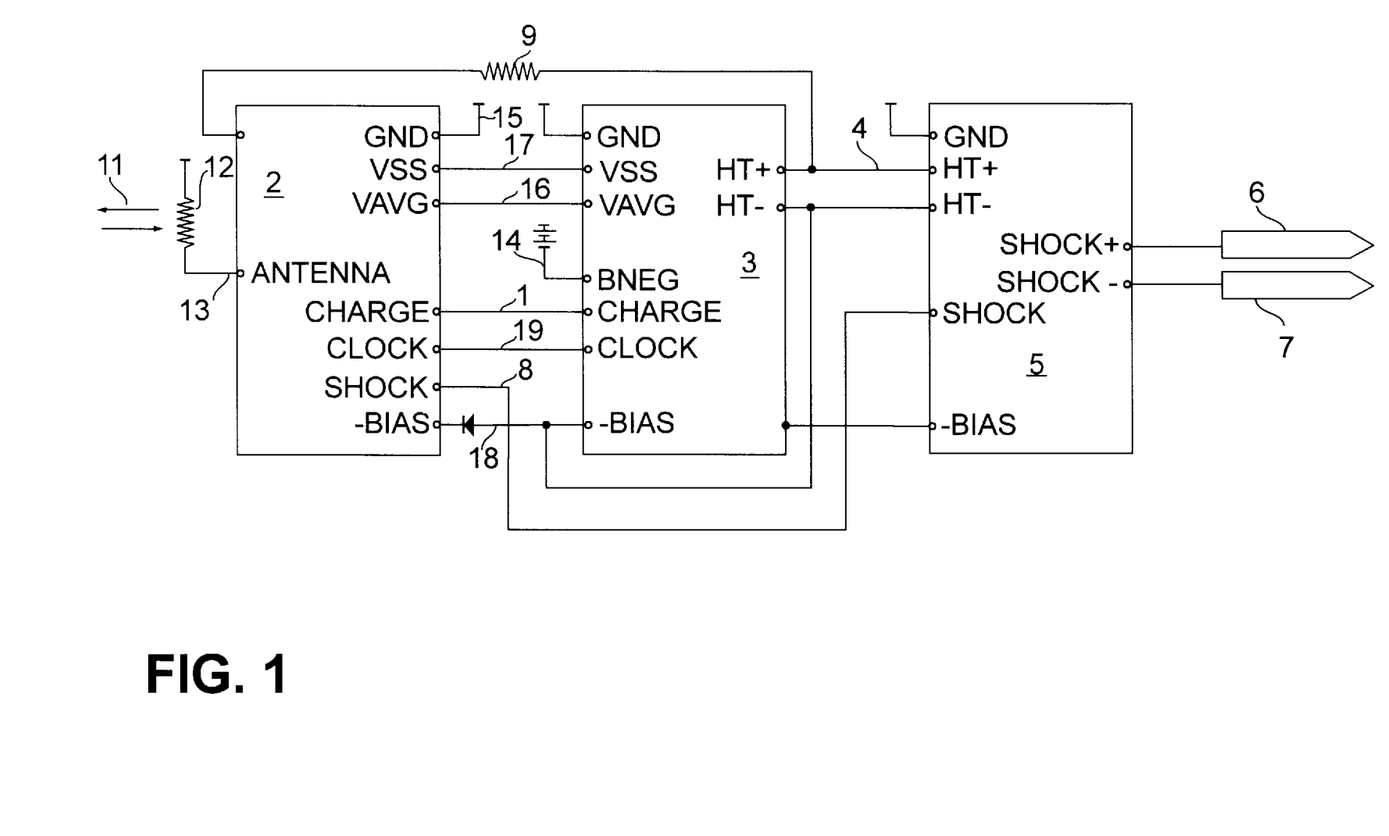
FIG. 1 is a schematic circuit diagram of a DC/DC converter in accordance with the present invention, applied to an implantable defibrillator.

FIG. 1 shows the DC/DC converter of the invention applied to an implantable defibrillator. Upon receipt of a charge command 1, from low power circuits 2, charger 3 operates to produce high voltage 4, which shock output circuits 5 in turn provide to shock electrode terminals 6 and 7 upon receipt of a shock command 8 from low power circuits 2.

Low power circuits 2 sample high voltage 4 through resistor 9 to determine when the load of charger 3 reaches a target voltage. In addition, low power circuits 2 assert the charge command 1 whenever those circuits 2 determine a need to shock, and the measured load voltage is less than the target voltage.

Low power circuits 2 communicate with an external device via an electromagnetic communication link 11, which includes an antenna 12 and an input/output port 13.

A battery 14 powers the device at a negative input voltage bneg. Ground 15 serves as a reference voltage (0 Volts) for all device signals, unless otherwise noted. The charger 3 converts the battery voltage to other supply voltages to power the rest of the device, including:

(i) high voltage supply 4 for shock generator, approximately 0.75 KV. High voltage supply 4 has a positive terminal HT+ and a negative terminal HT−. The negative terminal HT− is connected to a negative supply −Bias 18, not to ground. The positive terminal HT+ is passed to shock circuit 5.

(ii) average battery voltage Vavg 16, to operate charger 3 and to supply power to low power circuits 2. During operation of charger 3, the internal resistance of battery 14, together with high peak currents drawn during the inductor input phase, cause the battery terminal voltage to have large high-frequency components. The establishment of the average battery voltage Vavg permits reducing some fluctuation, preserves a minimum voltage supply for the other circuits, and reduces interference and increases headroom.

Low power circuits 2 also regulate Vavg 16 to produce logic supply vss 17, approximately −3.0 V, and then triple vss to produce negative bias supply −Bias 18, approximately −9.0 V (the most negative voltage in the device). When charger 3 operates, it brings −bias to a more negative voltage as will be shown below.

Referring still to FIG. 1, low power circuits 2 provide pacing, sensing in a conventional manner, and control charger 3 and shock generator 5. They operate between ground 15 and −Bias 18. Because the value of the normal pacing voltage is between these two supply voltages, low power circuits 2 can generate and measure pacing and sensing signals directly, without level-shifting. Since charger 3 operates between ground and a negative input voltage bneg, the low power circuits 2 also can control charger 3 without an additional inverted voltage supply. If charger 3 instead operated between ground and some positive voltage, the device would need to invert battery voltage to produce a pacing voltage.

As shown in FIG. 1, low power circuits 2 provide a clock signal 19 to charger 3, typically at a frequency substantially below the operating frequency of communication link 11.

Figure 2:
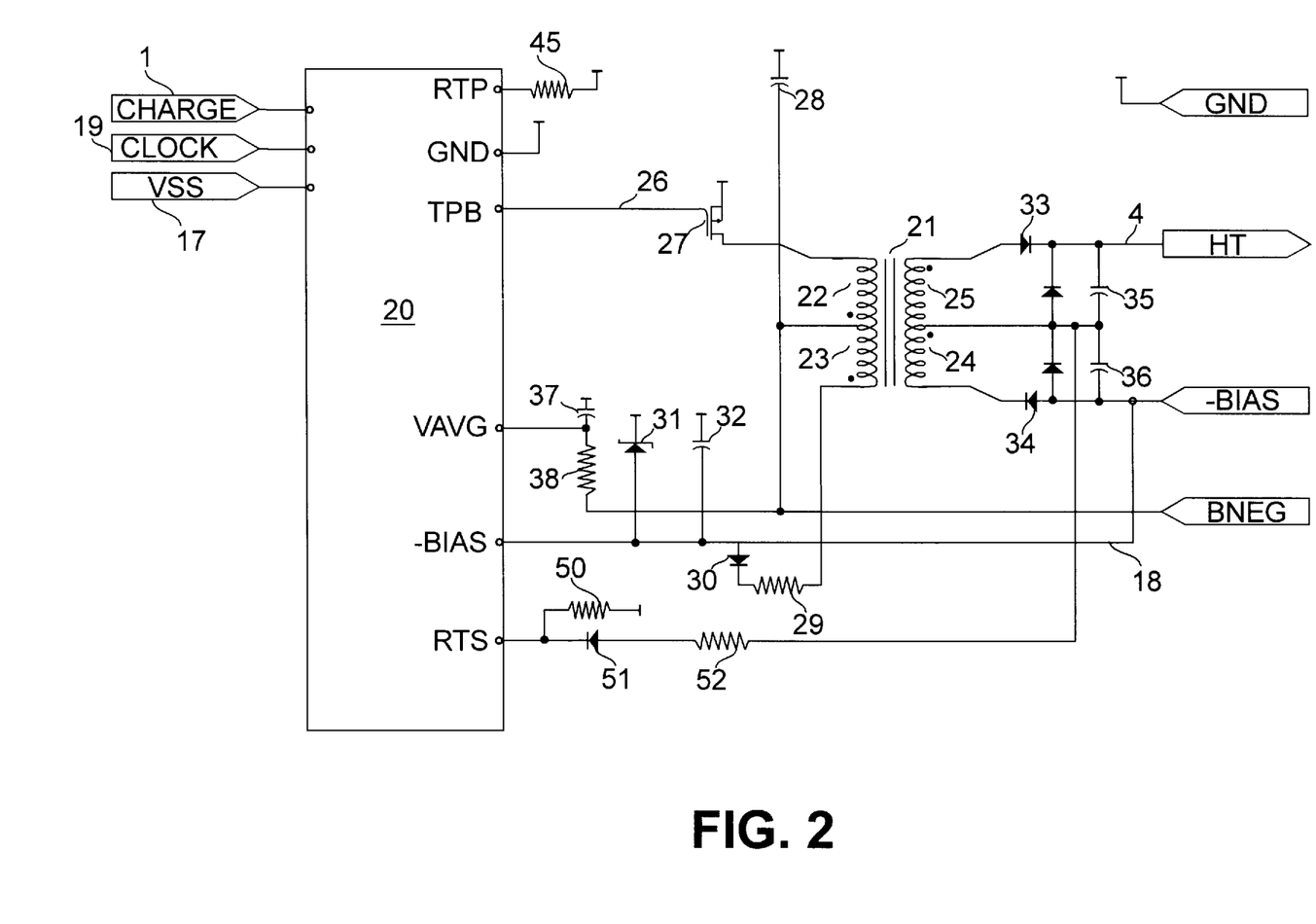
FIG. 2 is a schematic circuit diagram of the charging circuit of FIG. 1.

Referring to FIG. 2, charger 3 in FIG. 1 includes a timer at 20 together with various discrete components.

In a preferred embodiment, charger 3 has an inductive storing means that is a transformer 21. One suitable transformer 21 is one wound preferably on an RM-5 pot core made of N48 ferrite from Siemens, with Al of 63 nHy, with a primary winding 22 of 13 turns, boost winding 23 of 49 turns, and high voltage windings 24 and 25 of 80 turns each.

When timer 20 pulls signal tpb at lead 26 to a low state, this begins the input phase. Signal tpb turns on transistor 27, applying the battery voltage from ground to bneg across primary winding 22, so that the current ramps up in that winding 22. Capacitor 28 lowers battery ripple due to battery internal impedance. Also during the input phase, winding 23 multiplies the battery voltage, and resistor 29 and diode 30 further charge the −bias supply, clamped to approximately −15 V by zener diode 31, and filtered by capacitor 32. During the input phase, diodes 33 and 34 are reverse biased, so no energy is transferred to the output load, namely storage capacitors 35 and 36.

When timer 20 raises signal tpb at 26 to a high state, this begins the output phase. Signal tpb turns off transistor 27, interrupting the input current in primary winding 22. Output current then flows in secondary windings 24 and 25, charging load capacitors 35 and 36 through diodes 33 and 34. The voltage across windings 24 and 25 rises until diodes 33 and 34 clamp it to the voltage stored on capacitors 35 and 36 respectively.

The slope of the increasing current ramp during the input phase is equal to the battery voltage Vp, divided by the inductance Lp of winding 22. Thus the peak current Ip in winding 22 is Ip=Vp*Tp/Lp, where Tp is the duration of the input phase. The ratio of the peak current Is in windings 24 and 25 to the peak current Ip in winding 22 is equal to the number of turns Np in winding 22, divided by the sum Ns of the number of turns in windings 24 and 25. The slope of the decreasing current ramp during output phase is equal to the total voltage Vs on capacitors 35 and 36, divided by the total inductance Ls of windings 24 and 25 combined. Remembering that $L=Al*N^2$ for any winding, then Ts=(Ns/Np)*(Vp/Vs)*Tp, where Ts is the time necessary for the energy in the inductor to fall to zero during the output phase. Thus, for fixed input phase duration Tp, Ts is directly proportional to input source voltage Vp and inversely proportional to output load voltage Vs.

Referring to FIG. 2, capacitor 37 and resistor 38 produce supply Vavg from the battery voltage.

Figure 3:
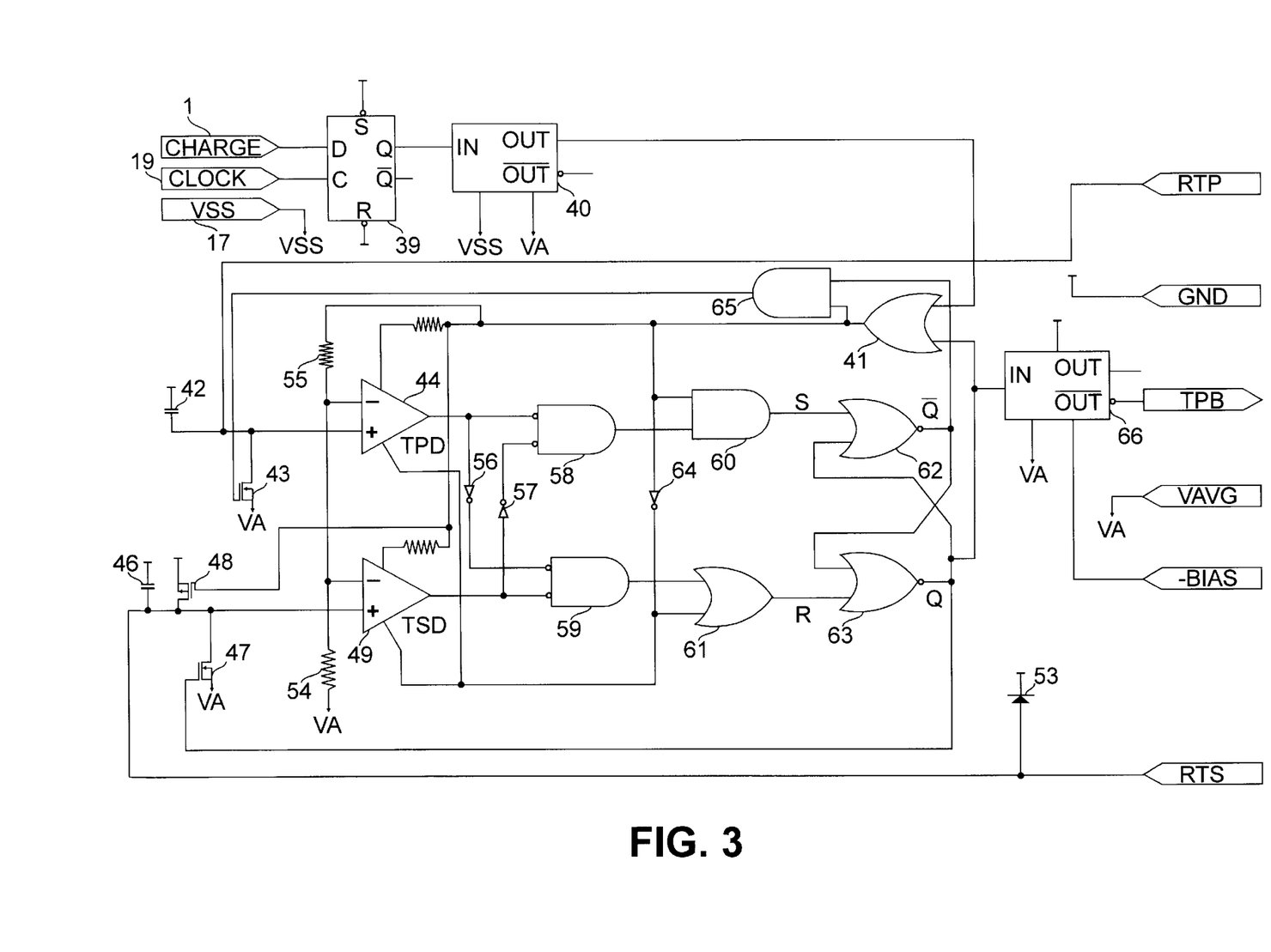
FIG. 3 is a schematic circuit diagram of the timer of FIG. 1.

FIG. 3 shows the detailed timer 20 circuitry. Timer control signals 1 and 19 and latch 39 operate between ground and vss at 17, since running as much circuitry as possible on a low voltage reduces power consumption. Timer output signal tpb at 26 operates between ground and −bias, since operating switch 27 in FIG. 2 at high gate-source voltage reduces the switch on-resistance. The rest of the timer circuitry in FIG. 3 operates between ground and Vavg, illustrated as "VA" in FIG. 3, for two reasons. First, this circuitry operates at high frequency and thus consumes relatively high current. Operating this from Vavg instead of vss reduces the load requirement on the vss regulator. Second, analog timing components operate over a range from Vavg to vdd for reasons explained below. It is advantageous for the circuitry driving and measuring voltages on these components also to operate over this range.

Timer logic is implemented preferably in complementary-symmetry metal-oxide semiconductor (CMOS) technology so that it draws no current when not enabled. Furthermore the circuit removes bias current to comparators 44 and 49, and to resistor divider 54 and 55, when not enabled. It also insures that there is no charging current to capacitors 42 and 46 when not enabled.

In FIG. 3, the timer includes a circuit for selectively enabling charger operation, consisting of latch 39, level shifter 40, and gate 41. Latch 39 can only change state at or below the frequency of clock 19, regardless of the width of the charge request signal at 1. Level-shifter 40 adapts the vss-level signal at the output of latch 39 to a Vavg-level signal to operate timer logic. When the output of level-shifter 40 is high, this enables the converter.

The timer also includes logic means to operate first and second monostable means alternately and repeatedly, to form an astable oscillator. The logic means is a logic circuit including gates 56 through 65 in FIG. 3. This circuit logic includes a set/reset latch comprising gates 62 and 63. When the Q output of the latch, at the output of gate 63, is high, this closes primary current switch 27 in FIG. 2 via level-shifter 66. Thus a high Q output corresponds to the converter input phase, and a high Q-bar ($\overline{Q}$) output at the output of gate 62 corresponds to the converter output phase. The level-shifter 66 enables driving switch 27 from the −Bias supply.

The output of gate 41 enables astable operation. Gate 41 insures that if the output of gate 40 goes low, to stop astable operation, while the converter is in the input phase, then the converter completes the input phase in progress before stopping. This insures that each time the converter cycles, it provides a maximum amount of energy to the load capacitors, improving converter efficiency.

Gate 60 prevents any signal from setting the latch (preventing input phase), unless gate 41 has enabled astable operation. Similarly gate 61 and inverter 64 insure the latch is reset (forcing output phase), unless gate 41 has enabled astable operation.

Via inverter 57 and gate 58, a high level at comparator 49 output TSD will set the latch (ending the output phase) provided there is a low level at comparator 44 output TPD. Similarly, via inverter 56 and gate 59, a high level at TPD will reset the latch (ending the input phase) provided there is a low level at TSD. Gates 58 and 59 block any setting or resetting when there is a high level on both TPD and TSD.

To complete the description of the logic means, gate 65 provides a high level when astable operation is enabled and the latch is reset (output phase).

The timer includes a threshold means, e.g., a resistive divider 54, 55, which sets a comparator threshold for two monostable circuits, discussed below, to a preset fraction of average battery voltage when the charger is enabled.

The timer also includes first monostable means for timing input phase duration. The first monostable means may be, for example, a monostable circuit that, during enabled astable operation controls the input phase duration by an RC and comparator network. One such circuit includes a timing capacitor 42, reset switch 43, and comparator 44, all shown in FIG. 3, and resistor 45 shown in FIG. 2. Assuming astable operation is enabled: Switch 43 holds timing capacitor 42 charged to Vavg during the output phase. At the start of the input phase, resistor 45 discharges capacitor 42 toward ground. When the negative terminal of capacitor 42 reaches the threshold voltage set by resistors 54 and 55, comparator 44 output TPD goes high, resetting the latch 62, 63 as explained above, thus ending the input phase and starting the output phase. During input phase, capacitor 42 discharges to a fixed fraction of its initial voltage via a fixed resistor; thus its period is independent of that initial voltage.

The timer further includes second monostable means for timing output phase duration. The second monostable means may be, for example, a monostable circuit that, during astable operation, controls the duration of the output phase using an RC network and a comparator. One suitable circuit includes a timing capacitor 46, reset switches 47 and 48, diode 53 and comparator 49, all shown in FIG. 3, and resistor 50, diode 51, and resistor 52 all shown in FIG. 2. Assuming astable operation is enabled: Switch 47 holds timing capacitor 46 charged to Vavg during the input phase. At the start of the output phase, resistor 50 discharges capacitor 46 toward ground, and resistor 52 in series with diode 51 also discharges capacitor 46 toward ground. When the negative terminal of capacitor 46 reaches the threshold voltage set by resistors 54 and 55, comparator 49 output TSD goes high, setting the latch 62, 63 as explained above, thus ending the output phase and starting the input phase.

In the absence of any current through resistor 52, capacitor 46 discharges to a fixed fraction of its initial voltage via a fixed resistor 50, thus its period is independent of that initial voltage. In practice, capacitor 46 and resistor 50 are selected so that the astable frequency of the converter is always substantially higher than the operating frequency of communication link 11 which is approximately 8 KHz in this example. Any current in resistor 52 will only speed up the converter.

When the load capacitors 35 and 36 are charged to a few tens of volts, resistor 52 provides current to discharge capacitor 46, this current being essentially directly proportional to capacitor output voltage at the junction of energy storage capacitors 35 and 36, and substantially greater than the current in resistor 50, so that resistor 52 alone essentially determines the duration of the output phase timed by this circuit. Since the threshold voltage at the junction of resistors 54 and 55 is a fraction of battery voltage, and since the slope of the discharge of capacitor 46 is proportional to output load voltage, then the output phase duration is directly proportional to battery voltage and inversely proportional to output voltage.

| TABLE SHOWING TYPICAL COMPONENT VALUES | | | |
|---|---|---|---|
| Component | Type | Value | Notes |
| 9 | resistor | 39 M | 1 KV |
| 14 | battery | 6.4 V | low esr |
| 27 | p-channel MOSFET | 0.3 Ohm, 60 V | IRFU 9024 |
| 28 | tantalum capacitor | 10 μF, 10 V | low esr |
| 29 | resistor | 0.68 K | |
| 30 | ultrafast recovery | 400 PIV, 1.0 A | BYV26C |

-continued

TABLE SHOWING TYPICAL COMPONENT VALUES

| Component | Type | Value | Notes |
|---|---|---|---|
| 31 | diode zener diode | 15 V | |
| 32 | tantalum capacitor | 1.0 µF, 50 V | |
| 33, 34 | ultrafast recovery diode | 600 PIV, 1.0 A | BYV26E |
| 35, 35 | aluminum electrolytic capacitor | 250 µF, 360 V | |
| 37 | tantalum capacitor | 10 µF, 10 V | |
| 38 | resistor | 33 Ohm | |
| 42, 46 | integrated capacitor | 40 pF | |
| 45 | resistor, select on test | 0.20 M to 0.50 M | sets input phase duration |
| 50 | resistor | 1.0 M | |
| 51, 53 | small signal diode | 20 PIV, 1.0 A | IN41418 |
| 52 | resistor | 2.5 M | 500 V |

Although the invention has been described with reference to a particular embodiment, it is to be understood that this embodiment is merely illustrative of the application of the principles of the invention. Numerous other modifications may be made and other arrangements may be devised without departing from the spirit and scope of the present invention.

I claim:

1. A DC/DC converter comprising:

an inductor having an input current and an output current;

a switch having an open condition to disable the inductor input current and a closed condition to enable the inductor input current to store energy in the inductor;

a diode for enabling the inductor output current to discharge energy stored in the inductor to a load in response to the inductor input current being substantially zero;

a timing control circuit to cycle repeatedly the switch to close for a first duration and then to open for a second duration;

output compensating means for adjusting said second duration in inverse proportion to an output load voltage produced by the inductor output current into the load;

wherein said timing control circuit further comprises:

a first monostable circuit to provide said first duration;

a second monostable circuit, including said output compensating means, to provide said second duration; and logic means for alternately and repeatedly operating said first and second monostable circuits to form an astable oscillator with a period essentially equal to the sum of said first and second durations.

2. The DC/DC converter of claim 1 wherein said second monostable circuit further comprises:

a timing capacitor;

means for resetting said timing capacitor to a first preset voltage when said logic means does not operate said second monostable circuit;

a threshold means for determining when the voltage across said timing capacitor reaches a preset threshold voltage, said output compensating means comprising means for charging or discharging said timing capacitor toward said threshold voltage at a current essentially proportional to the output load voltage, means for indicating completion of said second duration to said logic means, activated by said threshold means.

3. The DC/DC converter of claim 2, wherein said means for charging or discharging comprises a resistor connected between the output load voltage and the terminal of the timing capacitor connected to said threshold means.

4. The DC/DC converter of claim 1 wherein the output compensating means adjusts the second duration as a function of an average output load voltage.

5. The converter of claim 1 wherein the output compensating means adjusts the second duration as a function of a peak output load voltage.

6. A DC/DC converter comprising:

an inductor having an input current and an output current;

a switch having an open condition to disable the inductor input current and a closed condition to enable the inductor input current to store energy in the inductor;

a diode for enabling the inductor output current to discharge energy stored in the inductor to a load in response to the inductor input current being substantially zero;

a timing control circuit to cycle repeatedly the switch to close for a first duration and then to open for a second duration;

output compensating means for adjusting said second duration in inverse proportion to an output load voltage produced by the inductor output current into the load;

an input compensating means for adjusting said second duration in direct proportion to an input source voltage;

wherein said timing control circuit further comprises:

a first monostable circuit to provide said first duration;

a second monostable circuit, including said output compensating means and said input compensating means, to provide said second duration; and logic means for alternately operating said first and second monostable circuits to form an astable oscillator with a period essentially equal to the sum of said first and second durations.

7. The DC/DC converter of claim 6 wherein said first duration is a fixed preset value.

8. The DC/DC converter of claim 6 wherein said switch is connected in series between a positive terminal of an input source voltage and the inductor.

9. The DC/DC converter of claim 6 wherein said second monostable circuit further comprises:

a timing capacitor;

means for resetting said timing capacitor to a first preset fraction of said input source voltage when said logic means does not operate said second monostable circuit;

threshold means including said input compensating means for determining when the voltage across said timing capacitor reaches a threshold voltage equal to a preset fraction of said input source voltage;

said output compensating means comprising means for charging or discharging said timing capacitor toward said threshold voltage with a current essentially proportional to the output load voltage; and means for indicating completion of said second duration to said logic means, activated by said threshold means.

10. The DC/DC converter of claim 9, wherein said means for charging or discharging comprises a resistor connected between the output load voltage and the terminal of the timing capacitor connected to said threshold means.

11. A DC/DC converter comprising:

inductive means for storing energy having an inductor input current from an input source voltage and an inductor output current to an output load voltage;

switch means having an open state and a closed state for selectively enabling the inductor input current only during the closed state;

diode means for enabling the inductor output current only when the inductor input current is substantially zero;

timing means for repeatedly cycling said switch means to close for a first duration and then to open for a second duration, wherein said second duration is inversely related to a voltage produced by the inductor output current into an output load;

wherein said timing means further comprises:
first monostable means for timing said first duration;
second monostable means for timing said second duration in inverse relation to said output load voltage; and
logic means for alternately and repeatedly operating said first and second monostable means to form an astable oscillator with a period essentially equal to the sum of said first and second durations.

12. The converter of claim 11 where said second monostable means further comprises means for charging or discharging a timing capacitor toward a preset threshold voltage at a current essentially proportional to the output load voltage; and means for indicating completion of said second interval to said logic means in response to said timing capacitor reaching said preset threshold voltage.

13. The converter of claim 12, where said means for charging or discharging further comprises a resistor connected between the output load voltage and a terminal of the timing capacitor.

14. The converter of claim 11 wherein said second monostable means further comprises:

a timing capacitor;

means for resetting said timing capacitor to a first preset fraction of said input source voltage, when said logic means does not operate said second monostable means;

threshold means for determining when the voltage across said timing capacitor reaches a threshold voltage equal to a preset fraction of said input source voltage;

means for charging or discharging said timing capacitor toward said threshold voltage at a current essentially proportional to output load voltage; and means for indicating completion of said second interval to said logic means in response to said timing capacitor voltage being at threshold.

15. The converter of claim 13, wherein said means for charging or discharging further comprises a resistor connected between the output load voltage and the terminal of the timing capacitor connected to said threshold means.

16. A method for transferring energy from an input source voltage to an output load having a higher voltage than the input source comprising:

providing an inductor;

selectively enabling an inductor input current to flow from said input source voltage for a first duration to store energy in the inductor, and disabling the inductor input current for a second duration;

enabling an inductor output current to flow from the inductor to discharge energy to the output load only when the inductor input current is substantially zero;

adjusting said second duration in inverse proportion to the output load voltage produced by the inductor output current and in direct proportion to the input source voltage;

restricting the selective enabling and disabling of the inductor input current to a fundamental frequency above a preset threshold by providing a timing capacitor to control the second duration and simultaneously charging or discharging the timing capacitor toward a preset threshold voltage with current essentially independent of the output load voltage; and indicating completion of said second interval in response to the charge on the timing capacitor reaching said threshold.

* * * * *